United States Patent
Kubo et al.

(10) Patent No.: US 11,171,932 B2
(45) Date of Patent: Nov. 9, 2021

(54) DATA TRANSMITTING APPARATUS, DATA RECEIVING APPARATUS, METHOD AND PROGRAM

(71) Applicants: OMRON HEALTHCARE CO., LTD., Muko (JP); OMRON Corporation, Kyoto (JP)

(72) Inventors: Nobuo Kubo, Kyoto (JP); Toru Deno, Kyoto (JP); Hideki Kondo, Kyoto (JP)

(73) Assignees: OMRON HEALTHCARE CO., LTD., Kyoto (JP); OMRON CORPORATION, Kyoto (JP)

( * ) Notice: Subject to any disclaimer, the term of this patent is extended or adjusted under 35 U.S.C. 154(b) by 137 days.

(21) Appl. No.: 16/747,630

(22) Filed: Jan. 21, 2020

(65) Prior Publication Data
US 2020/0162435 A1     May 21, 2020

Related U.S. Application Data

(63) Continuation of application No. PCT/JP2018/028827, filed on Aug. 1, 2018.

(30) Foreign Application Priority Data

Aug. 9, 2017  (JP) .............................. JP2017-154765

(51) Int. Cl.
*H04L 29/06*       (2006.01)
*A61B 5/00*        (2006.01)
(Continued)

(52) U.S. Cl.
CPC .......... *H04L 63/0428* (2013.01); *A61B 5/002* (2013.01); *A61B 5/021* (2013.01);
(Continued)

(58) Field of Classification Search
CPC ... H04L 63/0428; H04L 9/0872; H04L 69/22; H04L 2209/80; G06F 21/602
See application file for complete search history.

(56) References Cited

U.S. PATENT DOCUMENTS 6,742,116 B1    5/2004  Matsui et al.
8,984,646 B2 *  3/2015  Ohno ................. H04N 21/4367
                                                    726/26
(Continued)

FOREIGN PATENT DOCUMENTS

JP     2000-115153 A    4/2000
JP     2000-224158 A    8/2000
(Continued)

OTHER PUBLICATIONS

English translation of Official Communication issued in International Patent Application No. PCT/JP2018/028827, dated Feb. 13, 2020.
Official Communication issued in International Patent Application No. PCT/JP2018/028827, dated Nov. 6, 2018.

*Primary Examiner* — Shawnchoy Rahman
(74) *Attorney, Agent, or Firm* — Keating and Bennett, LLP

(57) ABSTRACT

A data transmitting apparatus include a measurement control unit to measure an amount relating to biological information; an encryption key generation control unit to generate, as an encryption key, information calculated from first shared information and second shared information that is shared with a receiving apparatus; an encryption control unit to encrypt the biological information with the encryption key and generate encryption data; a packet generation control unit to generate a one-way transmission packet that includes the first shared information and the encryption data; and a transmitter to transmit the packet.

13 Claims, 8 Drawing Sheets

(51) Int. Cl.
- *A61B 5/021* (2006.01)
- *A61B 5/024* (2006.01)
- *G06F 21/60* (2013.01)
- *H04L 9/08* (2006.01)
- *H04W 12/033* (2021.01)
- *H04W 12/041* (2021.01)
- *H04W 12/0471* (2021.01)
- *H04W 4/80* (2018.01)
- *H04L 29/08* (2006.01)

(52) U.S. Cl.
CPC ........ *A61B 5/02416* (2013.01); *G06F 21/602* (2013.01); *H04L 9/0872* (2013.01); *H04L 69/22* (2013.01); *H04W 12/033* (2021.01); *H04W 12/041* (2021.01); *H04W 12/0471* (2021.01); *H04L 67/12* (2013.01); *H04L 2209/80* (2013.01); *H04W 4/80* (2018.02)

(56) References Cited

U.S. PATENT DOCUMENTS

| | | | |
|---|---|---|---|
| 10,057,269 | B1 * | 8/2018 | Ellingson .............. G06F 16/951 |
| 2002/0025045 | A1 | 2/2002 | Raike |
| 2012/0201383 | A1 | 8/2012 | Matsuo |
| 2016/0029148 | A1 | 1/2016 | Jackson et al. |
| 2016/0029149 | A1 | 1/2016 | Morikawa et al. |
| 2016/0066212 | A1 | 3/2016 | Visweswara |
| 2016/0080372 | A1 | 3/2016 | Martin et al. |

FOREIGN PATENT DOCUMENTS

| | | |
|---|---|---|
| JP | 2002-111652 A | 4/2002 |
| JP | 2006-122610 A | 5/2006 |
| JP | 2011-120051 A | 6/2011 |
| JP | 5852620 B2 | 2/2016 |
| JP | 2016-519861 A | 7/2016 |
| JP | 2017-067735 A | 4/2017 |

* cited by examiner

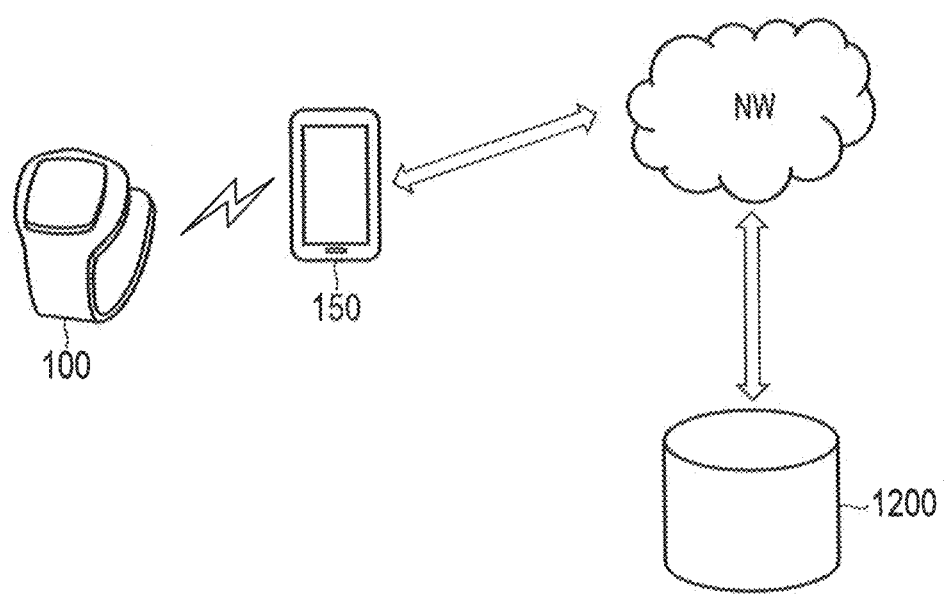
F I G. 12

DATA TRANSMITTING APPARATUS, DATA RECEIVING APPARATUS, METHOD AND PROGRAM

CROSS-REFERENCE TO RELATED APPLICATIONS

This application is a Continuation Application of PCT Application No. PCT/JP2018/028827, filed Aug. 1, 2018 and based upon and claiming the benefit of priority from Japanese Patent Application No. 2017-154765, filed Aug. 9, 2017, the entire contents of all of which are incorporated herein by reference.

FIELD

The present invention relates to a data transmitting apparatus, data receiving apparatus, method and program through one-way communication.

BACKGROUND

Blood pressure monitors provided with a function of transmitting blood pressure data to a user's portable information terminal have been introduced to the market. As a portable information terminal, a smartphone, a tablet terminal, or a notebook personal computer may be adopted. This function allows the user to view his/her own blood pressure measurement results under various conditions in list form on the portable information terminal. Typically, Near Field Communication technology, particularly Bluetooth (registered trademark) technology is used for transmission of the blood pressure data. In general, the Bluetooth communication (connection) can be realized on a smaller scale and in a power-saving manner in comparison to Wireless Local Area Network (WLAN) communication. The Bluetooth specification version 4.0 is also referred to as "Bluetooth Low Energy" (BLE), which can further reduce power consumption in comparison to the conventional scheme.

With BLE, a two-way communication known as "connection" can be performed. The connection, however, raises some issues. For example, the user is required to go through complicated operations for pairing; the communication procedure after the pairing is complicated; the mobile information terminal needs to support BLE; high-performance hardware (processor and memory) is required not only for the mobile information terminal but also for the blood pressure monitor; high development and/or evaluation costs are required; and an excessive amount of communication overhead makes the connection unsuitable for transmission of a small amount of data.

With BLE, one-way communication known as "advertising" can also be performed. Japanese Patent. No. 5852620 discloses a technique of transmission with any type of data included in the margin of the data field of an advertisement packet.

The use of advertising for the transmission of the blood pressure data eliminates the need for pairing and subsequent complicated communication procedures, thereby either solving or mitigating the above-mentioned issues. However, with the blood pressure monitor provided with only a one transmission function, control data cannot be transmitted for control from the portable information terminal to the blood pressure monitor, and the state of the portable information terminal (such as data reception state) cannot be referred to from the blood pressure monitor side.

In general, it is possible that the data wirelessly transmitted from the blood pressure monitor may be received by any data receiving apparatus other than the user's portable information terminal, depending on the propagation of the radio wave. If the blood pressure data is transmitted without being encrypted, there is the possibility that other people may view the user's blood pressure data Such leakage of information on the user's health condition needs to be prevented, and the security of the function of transmitting the blood pressure data must be enhanced. Furthermore, as described above, the blood pressure monitor, which is unable to refer to the data reception state at the portable information terminal if the blood pressure monitor is provided only with a one-way transmission function, may have to transmit packets with greater power than necessary in order to avoid any data loss at the portable information terminal. If this is the case, leakage of information indicating the user's health condition becomes even more likely to occur.

SUMMARY

A data transmitting apparatus according to an aspect of the present invention comprises a measurement control unit configured to measure an amount relating to biological information; an encryption key generation control unit configured to generate, as an encryption key, information calculated from first shared information and second shared information that can be shared with a receiving apparatus; an encryption control unit configured to encrypt the biological information with the encryption key and generate encryption data; a packet generation control unit configured to generate a one-way transmission packet that includes the first shared information and the encryption data; and a transmitter configured to transmit the packet.

With the above structure, targeted information (e.g., information of biological body, or hereinafter also referred to as "biological information") is encrypted, using the information calculated from the first shared information and the second shared information that can be shared with the receiving apparatus, as an encryption key. For example, if the identical second shared information (e.g., any identical numerical value (initial value)) is stored in advance in the receiving apparatus and the transmitting apparatus, and the first shared information (e.g., numerical values (event numerical values) relating to a quantifiable event) is shared between the data transmitting apparatus and the data receiving apparatus, the output value obtained through a calculation by inputting the first shared information and the second shared information will serve as an encryption key. This operation may be any operation as long as, for example, an input value establishes a correspondence with an output value. Ideally, an operation by which a one-to-one correspondence is established between an input value and an output value may be employed. If this is the case, an output value is determined uniquely for an input value, and conversely, an input value is determined uniquely for an input value. If not a one-to-one operation, the operation will suffice as long as output values are distributed in an appropriately discrete manner with respect to input values. In other words, different input values resulting in the same output value (e.g., an imperfect hash function) are acceptable. Alternatively, a perfect hash function may be adopted for the operation to obtain an output value.

The input value is determined from the first shared information and the second shared information. These may be determined through the same calculation. For security reasons, it is desirable that the operation for outputting an encryption key should be differentiated from the operation for outputting an input value.

Encrypted data is generated with the encryption key, and a one-way transmission packet containing the encryption data and first shared information is transmitted in this direction. That is, a packet is transmitted only from the data transmitting apparatus, and this apparatus is not designed to receive any packet. As described above, the targeted information is encrypted and transmitted with an encryption key calculated by inputting the first shared information and the second shared information. Thus, a data transmitting apparatus that realizes highly confidential transmission can be offered. For the encryption scheme, a common key encryption scheme can be adopted, and is not particularly limited to any specific encryption scheme.

In the data transmitting apparatus according to the above aspect, the first shared information, the second shared information and the calculated information do not include the biological information.

With the above structure, when generating a common encryption key from the first shared information, the second shared information and the calculated information at the data transmitting apparatus and the data receiving apparatus, the biological information is not used for the generation of an encryption key by the sensor of the data transmitting apparatus or data receiving apparatus. Thus, it is not necessary to attach the data transmitting apparatus and data receiving apparatus to the living body or to carry such apparatus around. By simply attaching only the data transmitting apparatus to a living body, the biological information for transmission can be acquired from the data transmitting apparatus, and can be encrypted and transmitted to the data receiving apparatus.

In the data transmitting apparatus according to the above aspect, the encryption key generation control unit associates the first shared information with a time and date, and the second shared information with a predetermined time and date.

With the above structure, the time and date is brought into correspondence with the first shared information, and transmitted in a packet to the data receiving apparatus. This allows the data transmitting apparatus and the data receiving apparatus to share the first shared information. As a result, the information (e.g., the time difference between the dates and times (also referred to as "elapsed hours" or "elapsed time period")), calculated from the second shared information (e.g., the same time and date determined in advance between the receiving apparatus and transmitting apparatus) and the first shared information (e.g., the time and date of the measurement of the amount relating to biological information), can be adopted as an encryption key. The time and date may be the point at which the biological information is measured at the data transmitting apparatus, or any time (in the future or past) as well. Moreover, the information may be the time/date information including not only the time but also the date, month and year. The time is considered as including information relating to the date, and is used in the same meaning as the time/date information.

In the data transmitting apparatus according to the above aspect, the time and date associated with the first shared information includes a time and date of measurement of the amount relating to the biological information.

With the above structure, an encryption key can be generated through a predetermined operation by adopting as shared information, for example, the information calculated from the same time (second shared information) shared between the receiving apparatus and transmitting apparatus and the time and date (first shared information of the measurement of the amount relating to the biological information.

In the data transmitting apparatus according to the above aspect, the information calculated from the first shared information and second shared information includes an elapsed time period from a time and date determined in accordance with the second shared information to the time and date associated with the first shared information.

With the above structure, an elapsed time period can be adopted as an encryption key, where the elapsed time period is a time difference between the same time and date (second shared information) determined in advance in the receiving apparatus and transmitting apparatus, and the time and date (first shared information) of the measurement of the amount relating to the biological information. Therefore, any arbitrary data (e.g., biological information) can be encrypted with an encryption key that is valid only between the data transmitting apparatus and the data receiving apparatus.

In the data transmitting apparatus according to the above aspect, the biological information includes at least one of blood pressure values or pulse.

With the above structure, the data transmitting apparatus can transmit the biological information based on the first shared information and the second shared information as an encryption key. In general, the biological information is time-series data of blood pressure values and/or pulse, which includes the acquisition time and date. Thus, a data transmitting apparatus that can securely transmit the targeted biological information can be offered.

In a data receiving apparatus according to the above aspect, a receiver configured to receive a one-way transmission packet that includes encryption data that is data that has been encrypted, and first shared information that can be shared with a transmitting apparatus; an encryption key determination control unit configured to determine, as an encryption key, information calculated from second shared information shared with the transmitting apparatus, based on the first shared information; and a decoding control unit configured to decode the encryption data included in the packet with the encryption key, and generate decoded data, wherein the decoded data includes biological information measured by the transmitting apparatus.

With the above structure, targeted information (e.g., biological information) is encrypted through the use, as an encryption key, of the information calculated from the first shared information and the second shared information shared with the data transmitting apparatus. The first shared information and second shared information may be numerical values. The first shared information and second shared information can be shared between the data transmitting apparatus and the data receiving apparatus by storing the same initial value (second shared information) in advance in the receiving apparatus and transmitting apparatus, and also by transmitting the event numerical values relating to a quantifiable event (first shared information). Both the data transmitting apparatus and the data receiving apparatus generate an encryption key in accordance with a determined operation based on the first shared information and the second shared information so that the data receiving apparatus can realize secure reception and decode the encryption data with this encryption key to obtain the targeted biological information.

In the data receiving apparatus according to the above aspect, the first shared information, the second shared information and the calculated information do not include the biological information.

With the above structure, when generating an encryption key that is common between the data receiving apparatus and the data transmitting apparatus, biological information is not used for generation of an encryption key in the sensor of either of the apparatuses. Thus, without the need to employ an encryption key that uses biological information, various usage forms are possible for the data receiving apparatus. For example, the data receiving apparatus need neither be attached to a living body nor carried around continually. As a result, the data receiving apparatus can send and receive the encryption data even when the apparatus is located at home.

In the data receiving apparatus according to the above aspect, the first shared information is a time and date of measurement of an amount relating to the biological information by the transmitting apparatus, and the encryption key determination control unit determines the encryption key from the second shared information, based on the time and date of the measurement of the amount relating to the biological information.

With the above structure, the time and date of the measurement of the amount relating to the biological information is prepared in a packet by the transmitting apparatus, and received by the data receiving apparatus, enabling the data transmitting apparatus and the data receiving apparatus to therefore share this time and date. The receiving apparatus and transmitting apparatus may adopt, as an encryption key, the information (e.g., elapsed time period that is the time difference between these dates and times) calculated from the same time and date (second shared information) determined in advance and the time and date (first shared information) of the measurement of the amount relating to the biological information. The time and date may be those of the measurement of the amount relating to the biological information by the data transmitting apparatus, or any time and date (in the future or past). Moreover, the information may be the time/date information that includes not only the time, but also the date, month and year. The time is considered as including information relating to the date, and is used for the same meaning as the time/date information.

In the data receiving apparatus according to the above aspect, the information calculated from the first shared information and the second shared information includes an elapsed time period from the time and, date determined in accordance with the second shared information and a time and date associated with the first shared information.

With the above structure, the elapsed time period from the time and date (second shared information) shared in advance between the receiving apparatus and transmitting apparatus to the time and date (first shared information) of the measurement of the amount relating to the biological information is defined as an encryption key. Since this elapsed time period is known only between the data receiving apparatus and the data transmitting apparatus, a data receiving apparatus that can securely exchange the biological information can be offered.

In the data receiving apparatus according to the above aspect, the biological information includes at least one of blood pressure values or pulse.

With the above structure, the decoded data is biological information obtained by the sensor of the data transmitting apparatus, such as a blood pressure value and/or pulse. The data receiving apparatus can decode the biological information through the use, as an encryption key, of the information generated based on the first shared information and the second shared information. In general, the biological information is time-series data of blood pressure values and/or pulse, which includes the acquisition time and date. Thus, a data receiving apparatus that can securely decode the targeted biological information can be offered.

The data transmitting apparatus according to the above aspect is a blood pressure monitor or pulse meter, and the data receiving apparatus is a portable information terminal.

With the above structure, biological information measured by a blood pressure monitor or pulse meter can be transmitted so that a portable information terminal can securely receive this biological information.

A packet generated by the data transmitting apparatus according to the above aspect is transmitted through a short-range wireless communication scheme.

With the above structure, the transmission from the data transmitting apparatus to the data receiving apparatus can be achieved with reduced power consumption and by less expensive devices in comparison to other wireless communication schemes, by adopting a short-range wireless communication scheme (e.g., BLE).

According to the present invention, it is possible to offer a data transmitting apparatus, data receiving apparatus, method, and program that can prevent leakage of data transmitted through one-way communication.

BRIEF DESCRIPTION OF THE DRAWINGS

FIG. 12 is a diagram illustrating an exemplary data transmission system including the data transmitting apparatus and the data receiving apparatus according to the embodiment.

DETAILED DESCRIPTION

The present embodiments have been made in light of the above circumstances. The object of the present embodiments is to provide a data transmitting apparatus, a data receiving apparatus, a method, and a program that can suppress leakage of data transmitted through one-way communication.

To address the above-described issues, the present embodiments may adopt the structures as described below.

An embodiment according to one aspect of the present invention (hereinafter also referred to as "the present embodiment") will be described below with reference to the drawings. In the following embodiments, the components with the same numerals assigned should be understood as components performing the same operations, and repeat explanations are avoided.

APPLICATION EXAMPLE

Figure 1:
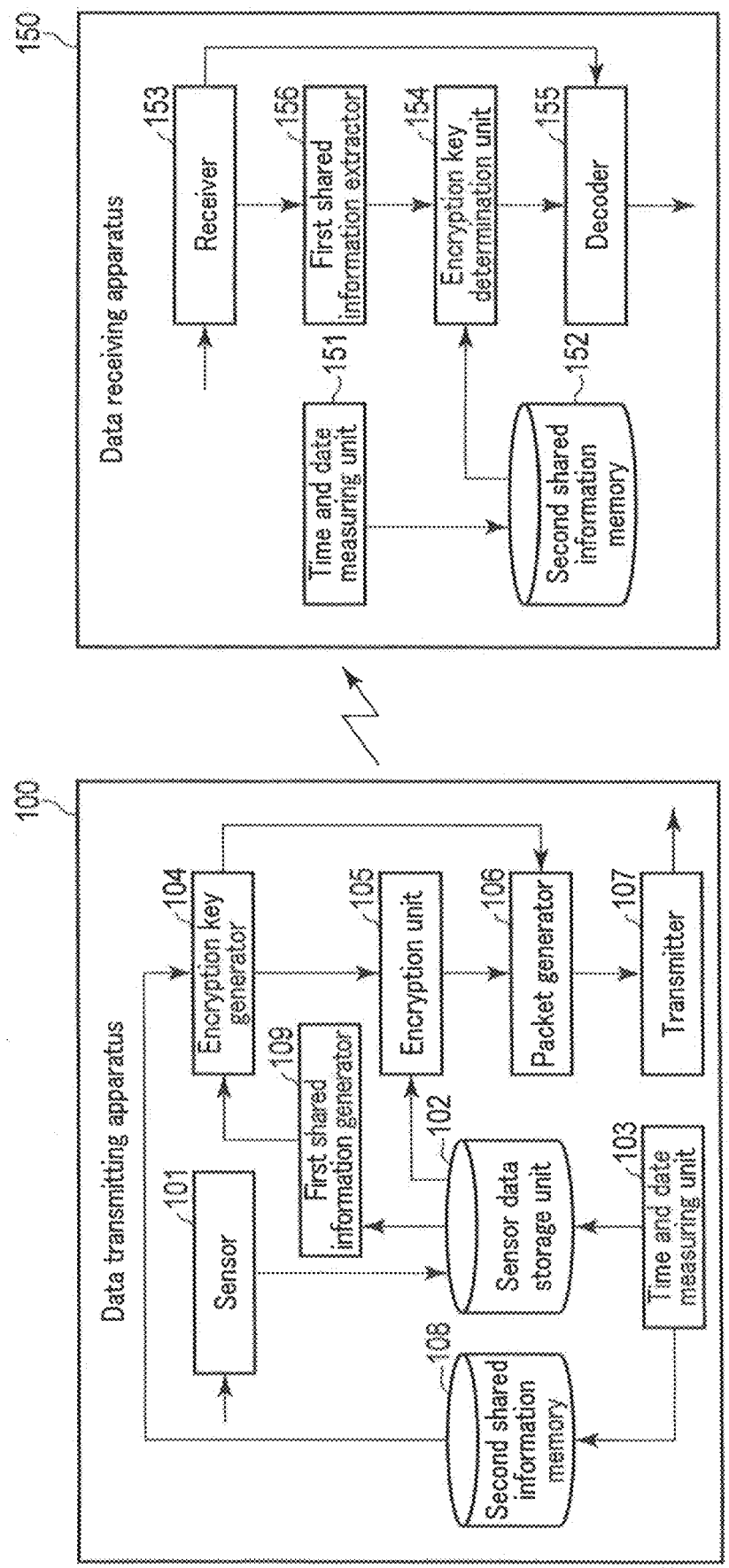
FIG. 1 is a diagram schematically illustrating an exemplary application of a data transmitting apparatus and a data receiving apparatus according to an embodiment.

First, an exemplary application of the present invention will be described with reference to FIG. 1. An exemplary application of a data transmitting apparatus 100 and a data receiving apparatus 150 according to the present embodiment is schematically illustrated in FIG. 1. The data transmitting apparatus 100 according to the present embodiment enters, into a sensor data storage unit 102, time-series sensor data in which the sensor data acquired from the living body by a sensor 101 is associated with the time by a time and date measuring unit 103. A first shared information generator 109 generates first shared information from the sensor data storage unit 102, and an encryption key generator 104 acquires second shared information from a second shared information memory 108. Based on the first shared information and second shared information of the data transmitting apparatus 100 and the data receiving apparatus 150, the encryption key generator 104 generates an encryption key, and an encryption unit 105 encrypts, with this encryption key, the transmission-targeted data (e.g., biological information) acquired from the sensor data storage unit 102. Next, a packet generator 106 generates a packet including the first shared information and encryption data, and a transmitter 107 transmits the generated one-way transmission packet (using, for example, BLE advertising). The encryption key generator 104 corresponds to the "encryption key generation control unit" of the present invention, and the encryption unit 105 corresponds to the "encryption control unit" of the present invention. The first shared information may be the time and date of acquiring (or detecting) sensor data by the sensor. The second shared information may be the time and date shared in advance between the data transmitting apparatus and the data receiving apparatus. To be more precise, the time and date of acquiring (or measuring and detecting) the sensor data by the sensor is the time and date of the sensor acquiring (or measuring and detecting) the biological information, which is the source of the sensor data. For the sake of convenience, these acquisitions are used in the same meaning in the following description and claims. It is preferable that the second shared information is designed to be set freely by the user. As a result, even when multiple data transmitting apparatuses and data receiving apparatuses are present, the possibility of the same encryption key being generated is reduced. Thus, even in the case where a data receiving apparatus that should not perform the decoding receives the first shared information, the possibility that this data receiving apparatus is able to decode the encryption data is reduced.

In the data receiving apparatus 150 according to the present embodiment, a receiver 153 receives a one-way transmission packet, and an encryption key determination unit 154 generates and determines an encryption key based on the first shared information (e.g., the time/date data of acquisition of sensor data by the sensor) extracted from the packet by a first shared information extractor 156 and the information included in a second shared information memory 152. The second shared information memory 152 stores the second shared information shared between the data receiving apparatus and the data transmitting apparatus (e.g., predetermined identical numerical values (serving as an initial value, such as time)). A decoder 155 can decode the encryption data received by the receiver 153 with the encryption key, which is generated by the encryption key determination unit 154, so that the data receiving apparatus can receive the targeted data acquired by the data transmitting apparatus. A time and date measuring unit 151 is employed when attaching the time/date data as the information relating to the second shared information stored in the second shared information memory 152. As a simple example, the time and date measuring unit 151 may be employed when a user enters the targeted time data in the second shared information memory 152 through the use of an input device.

A one-way transmission scheme from a data transmitting apparatus to a data receiving apparatus may be BLE advertising. A one-way transmission packet is generated by this communication scheme. Furthermore, the targeted data transmitted in the present embodiment may be biological information, and in particular, blood pressure values and/or pulse. The sensor data may be any data detectable by the sensor 101, and may be the number of steps and/or three-axis acceleration. Furthermore, biological information such as blood pressure values and/or pulse can also suffice if detectable by a sensor. A common key encryption method is adopted as the encryption scheme, and is not particularly limited to any specific encryption scheme. For example, Data Encryption Standard (DES) or Advanced Encryption Standard (AES) may be adopted. Moreover, the data transmitting apparatus may be a blood pressure monitor or a pulse meter, and the data receiving apparatus may be a portable information terminal such as a smartphone, a mobile phone, or a mobile personal computer.

As described above, the data transmitting apparatus 100 according to the present embodiment is configured to encrypt the targeted biological information with an encryption key calculated from the first shared information generated by the data transmitting apparatus 100 and the second shared information shared in advance between the receiving apparatus and the transmitting apparatus, and transmits a one-way transmission packet. The data receiving apparatus 150 is configured to decode the encryption data with the calculated information as an encryption key, where the information is calculated based on the first shared information that is included in the packet transmitted from the data transmitting apparatus 100, and the second shared information (e.g., any numerical values that are identical) that is shared in advance between the receiving apparatus and the transmitting apparatus. Thus, the data receiving apparatus 150 can obtain the same first shared information and second shared information as those of the data transmitting apparatus 100, and can therefore generate an encryption key through a calculation from such shared information. The same encryption key is obtained by the data transmitting apparatus 100 and by the data receiving apparatus 150. In other words, both the data transmitting apparatus 100 and the data receiving apparatus 150 can set an encryption key calculated based on the shared information, which includes the first shared information generated by the data transmitting apparatus 100 and the predetermined second shared information. For this reason, according to the present embodiment, an encryption key can be generated independently on the transmission side and the reception side, through the use of the first shared information generated by the data transmitting apparatus 100 and the second shared information (any numerical values that are identical) shared in advance by the receiving apparatus and the transmitting apparatus, and one-way transmission packets can be thereby transmitted to securely deliver information. As a result, the first shared information produces an effect on the encryption key greater than that generated by the encryption method adopting a shared encryption key corresponding to the second shared information only, thus realizing secure transmission of information with the method according to the present embodiment.

STRUCTURAL EXAMPLE (Hardware Structure)
<Data Transmitting Apparatus>

Next, an exemplary hardware structure of the data transmitting apparatus 100 according to the present embodiment will be described with reference to FIG. 2.

Figure 2:
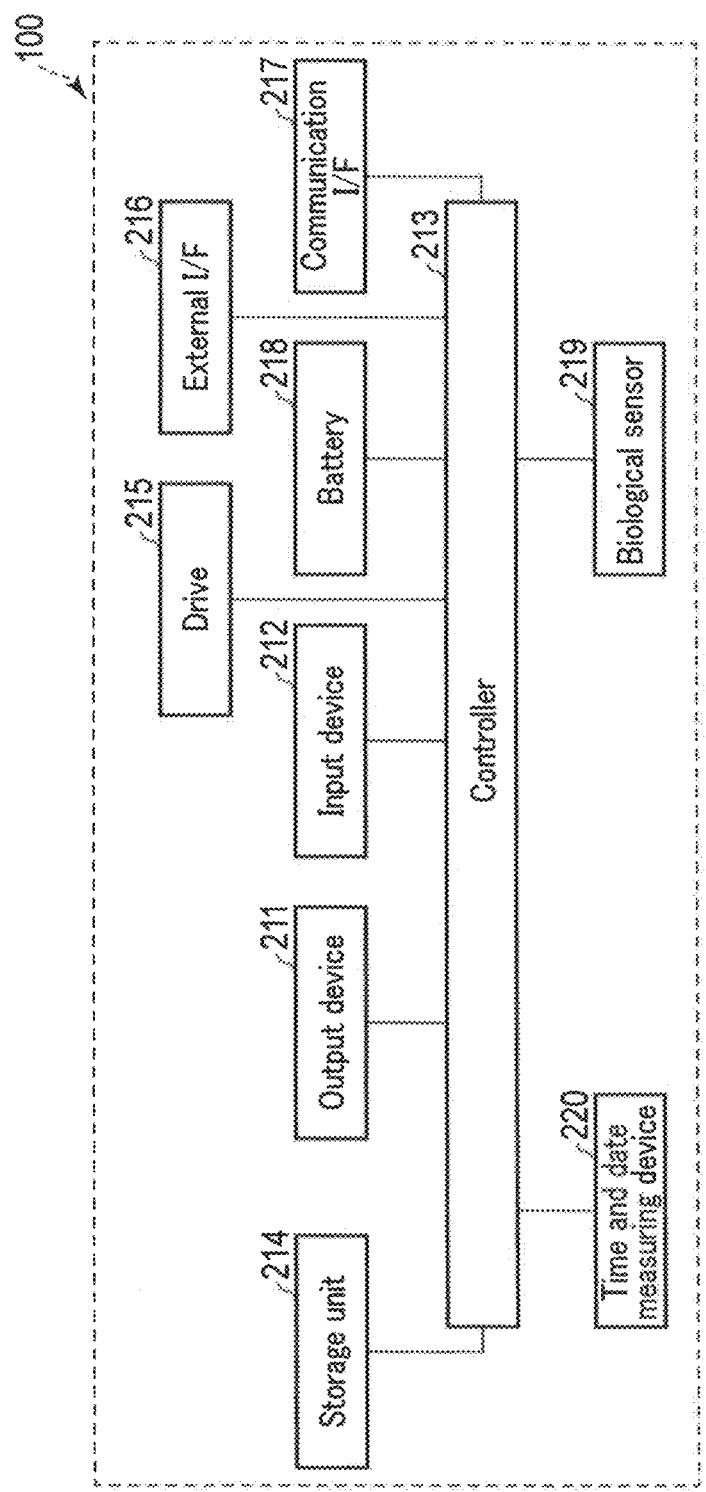
FIG. 2 is a diagram schematically illustrating an exemplary hardware structure of the data transmitting apparatus according to the embodiment.

As shown in FIG. 2, the data transmitting apparatus 100 according to the present embodiment includes a computer, in which an output device 211, an input device 212, a controller 213, a storage unit 214, a drive 215, an external interface 216, a communication interface 217, and a battery 218 are electrically connected to each other. Furthermore, the data transmitting apparatus 100 includes a biological sensor 219 and a time and date measuring device 220. The data transmitting apparatus 100 according to the present embodiment corresponds to the "data transmitting apparatus" of the present invention. In FIG. 2, the communication interface and external interface are described as "communication I/F" and "external I/F", respectively.

The controller 213 includes a central processing unit (CPU), a random access memory (RAM), a read only memory (ROM), and the like, and controls the structural components in accordance with the information processing. The storage unit 214 is, for example, an auxiliary storage device such as a hard disk drive or a solid state drive, and stores an encryption key generation and packet transmission control program to be implemented by the controller 213, the sensor data detected by the biological sensor 219, the targeted data scheduled for transmission, the second shared information, the time/date data measured by the time and date measuring device 220, and the like.

Figure 6:
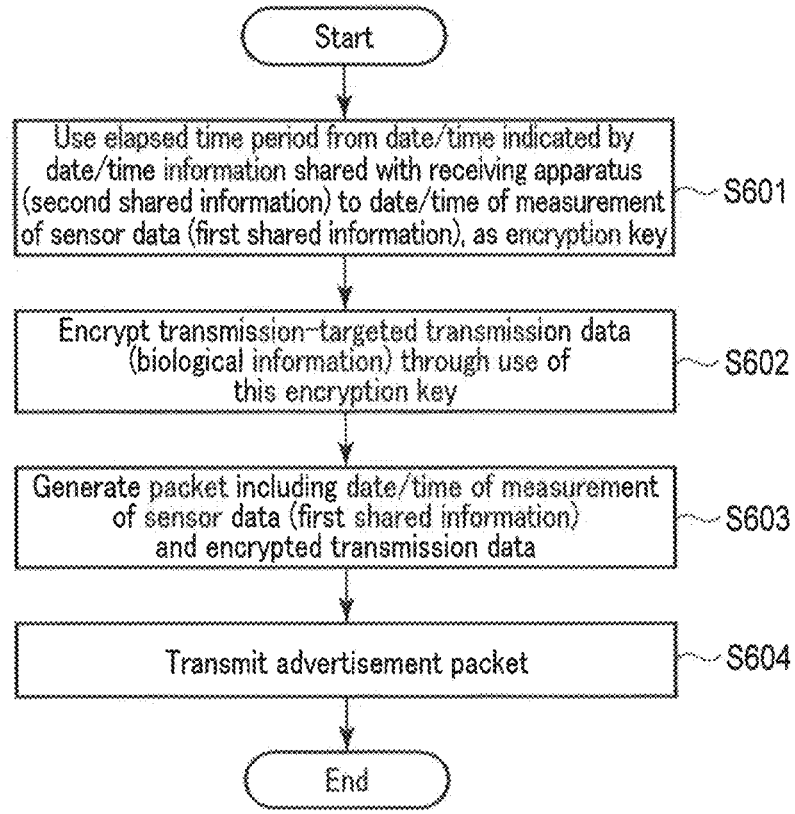
FIG. 6 is a diagram illustrating an exemplary processing procedure of the data transmitting apparatus according to the embodiment.

The encryption key generation and packet transmission control program is to implement the processing of generating an encryption key from the first shared information and second shared information, encrypting the targeted data with the generated encryption key, and transmitting the first shared information and the encryption data in a one-way transmission packet (FIG. 6). The targeted data may be biological information. The biological information may be time-series data of blood pressure values.

The communication interface 217 may be a short-range wireless communication (e.g., Bluetooth (registered trademark)) module, a wireless LAN module or the like, and is an interface for performing wireless communication via a network. The communication interface 217 is an interface for wirelessly connecting the data transmitting apparatus 100 to the data receiving apparatus 150. The communication interface 217 is controlled by the controller 213. The communication interface 217 is employed to receive packets including the encryption data generated by the controller 213 and to transmit the packets to the data receiving apparatus 150. The communication interface 217 cannot receive information from the data receiving apparatus 150, but can only transmit one-way transmission packets.

The input device 212 may be a device for inputting, such as a mouse and a keyboard. The output device 211 may be a device for outputting, such as a display and a speaker. The external interface 216 is a USB port or the like, and is an interface for establishing a connection to an external device such as a biological sensor 219 and/or time and date measuring device 220. In FIG. 2, the biological sensor 219 and the time and date measuring device 220 are not illustrated as being connected to the external interface 216. In the subsequent drawings such as FIG. 4, their connections to the blocks inside the controller 213 are illustrated, for the sake of simplicity, as being directly connected to the controller 213 so as to clarify the connections.

The storage unit. 214 accumulates information such as programs through an electrical, magnetic, optical, mechanical, or chemical action in a manner that a computer or other devices and machines can read the stored information such as programs. The data transmitting apparatus 100 may acquire from this storage unit 214 the encryption key generation and packet transmission control program, the sensor data detected by the biological sensor 219, the transmission-targeted data, the second shared information shared in advance between the data transmitting apparatus and the data receiving apparatus, and the time/date data measured by the time and date measuring device 220.

The drive 215 may be a compact disk (CD) drive, a digital versatile disk (DVD) drive or the like, and is a device for reading a program stored in a storage medium. The type of drive 215 may be appropriately selected according to the type of storage medium. The above-mentioned encryption key generation and packet transmission control program, sensor data detected by the biological sensor 219, the transmission-targeted data, and the time/date data measured by the time and date measuring device 220 may be stored in such a storage medium. Here, a disk type storage medium such as a CD and a DVD is illustrated as an example of the storage medium. The type of storage medium, however, is not limited to the disk type, but may be of any other type. Examples of the storage medium other than the disk type include a semiconductor memory such as a flash memory.

The battery 218 may be a rechargeable secondary battery. The battery 218 supplies power to every component incorporated in the main body of the data transmitting apparatus 100. The battery 218 supplies power, for example, to the output device 211, input device 212, controller 213, storage unit 214, drive 215, external interface 216, communication interface 217, biological sensor 219, and time and date measuring device 220.

The biological sensor 219 may be a blood pressure measuring device. If this is the case, the biological sensor 219 detects, for example, the pressure of the pressing cuff attached to the wrist of the user who is a living body, thereby detecting the blood pressure value of the living body. The biological sensor 219 outputs the blood pressure data (e.g., time-series data of blood pressure values) to the controller 213. The biological sensor 219 may be a pulse measuring device, or may measure a pulse together with the blood pressure.

The time and date measuring device 220 is a device for measuring time, which can measure the time and date. For example, the time and date measuring device 220 may be a clock including a calendar, which sends the current time/date information to the controller 213.

With regard to the specific hardware structure of the data transmitting apparatus 100, structural components may be omitted, replaced, and added as appropriate, according to the embodiment. For example, the controller 213 may include multiple processors. The data transmitting apparatus 100 may be constituted by multiple information processing apparatuses. In addition, the data transmitting apparatus 100 may be an information processing apparatus specifically designed for services provided, or otherwise may be a general-purpose desktop personal computer (PC), tablet PC, or the like.

<Data Receiving Apparatus>

Next, an exemplary hardware structure of the data receiving apparatus 150 according to the present embodiment will be described with reference to FIG. 3. The hardware structure of the data receiving apparatus 150 is basically the same as the data transmitting apparatus 100.

Figure 3:
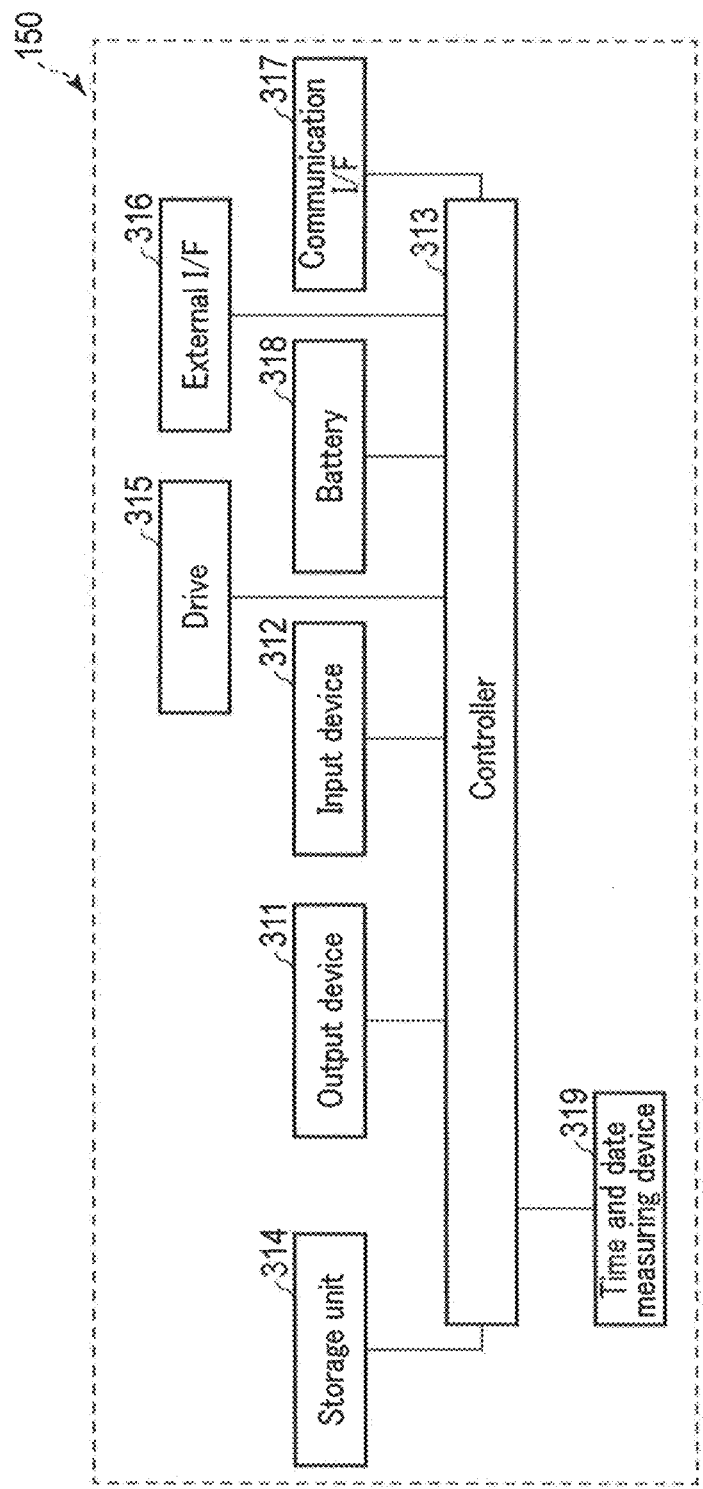
FIG. 3 is a diagram schematically illustrating an exemplary hardware structure of the data receiving apparatus according to the embodiment.

As illustrated in FIG. 3, the data receiving apparatus 150 according to the present embodiment includes a computer in which an output device 311, an input device 312, a controller 313, a storage unit 314, a drive 315, an external interface 316, a communication interface 317, and a battery 318 are electrically connected to each other. Furthermore, the data receiving apparatus 150 includes a time and date measuring device 319. The data receiving apparatus 150 according to the present embodiment corresponds to the "data receiving apparatus" of the present invention. In FIG. 3, the communication interface and external interface are described as a "communication I/F" and "external I/F", respectively.

The controller 313 includes a central processing unit (CPU), a random access memory (RAM), a read only memory (ROM) and the like, and controls respective structural components in accordance with the information processing. The storage unit 314 is, for example, an auxiliary storage device such as a hard disk drive or a solid state drive, and stores an encryption key generation and data decoding control program to be implemented by the controller 313, the targeted data that has been received and decoded, the second shared information shared in advance between the data transmitting apparatus and data receiving apparatus, the time/date data measured by the time and date measuring device 319, and the like.

The encryption key generation and data decoding control program is to execute a process (FIG. 7) for generating an encryption key from the first shared information included in the packet and the second shared information shared in advance and decoding the encryption data included in the received one-way transmission packet, with the generated encryption key. The targeted data may be biological information. The biological information may be time-series data of blood pressure values.

The communication interface 317 is basically the same as the communication interface 217. A communication interface 317 is an interface for receiving data from the data transmitting apparatus 100. The communication interface 317 receives a packet from the data transmitting apparatus 100 and sends it to the controller 313.

The input device 312, output device 311, and external interface 316 are similar to the input device 212, output device 211, and external interface 216, respectively.

The storage unit 314 accumulates information such as programs through an electrical, magnetic, optical, mechanical, or chemical action in a manner that a computer or other device and machine can read the stored information such as programs. The data receiving apparatus 150 may acquire from this storage unit 314 the encryption key generation and data decoding control program, the targeted data that has been received and decoded, the second shared information shared in advance between the data transmitting apparatus and the data receiving apparatus, and the time/date data measured by the time and date measuring device 319.

The drive 315 may be a compact disk (CD) drive, a digital versatile disk (DVD) drive, or the like, and is a device for reading a program stored in a storage medium. The type of drive 315 may be appropriately selected according to the type of storage medium. The above-mentioned encryption key generation and data decoding control program, the sensor data detected by the time and date measuring device 319 and/or motion sensor 320, the targeted data that has been received and decoded, and the time/date data measured by the time and date measuring device 319 may be stored in this storage medium. Here, a disk type storage medium such as a CD and a DVD is illustrated as an example of the storage medium. The type of storage medium, however, is not limited to the disk type, but may be of any other type. Examples of the storage medium other than the disk type may include a semiconductor memory such as a flash memory.

The battery 318 is similar to the battery 218. The battery 318 supplies power to the components incorporated in the main body of the data receiving apparatus 150.

The time and date measuring device 319 is similar to the time and date measuring device 220.

With regard to the specific hardware structure of the data receiving apparatus 150, structural components may be omitted, replaced, and added as appropriate, according to the embodiment. For example, the controller 313 may include multiple processors. The data receiving apparatus 150 may be constituted by multiple information processing apparatuses. In addition, the data receiving apparatus 150 may be an information processing apparatus specifically designed for the provided service, or may otherwise be a general-purpose desktop personal computer (PC), tablet PC or the like.

(Software Structure)

<Data Transmitting Apparatus>

Figure 4:
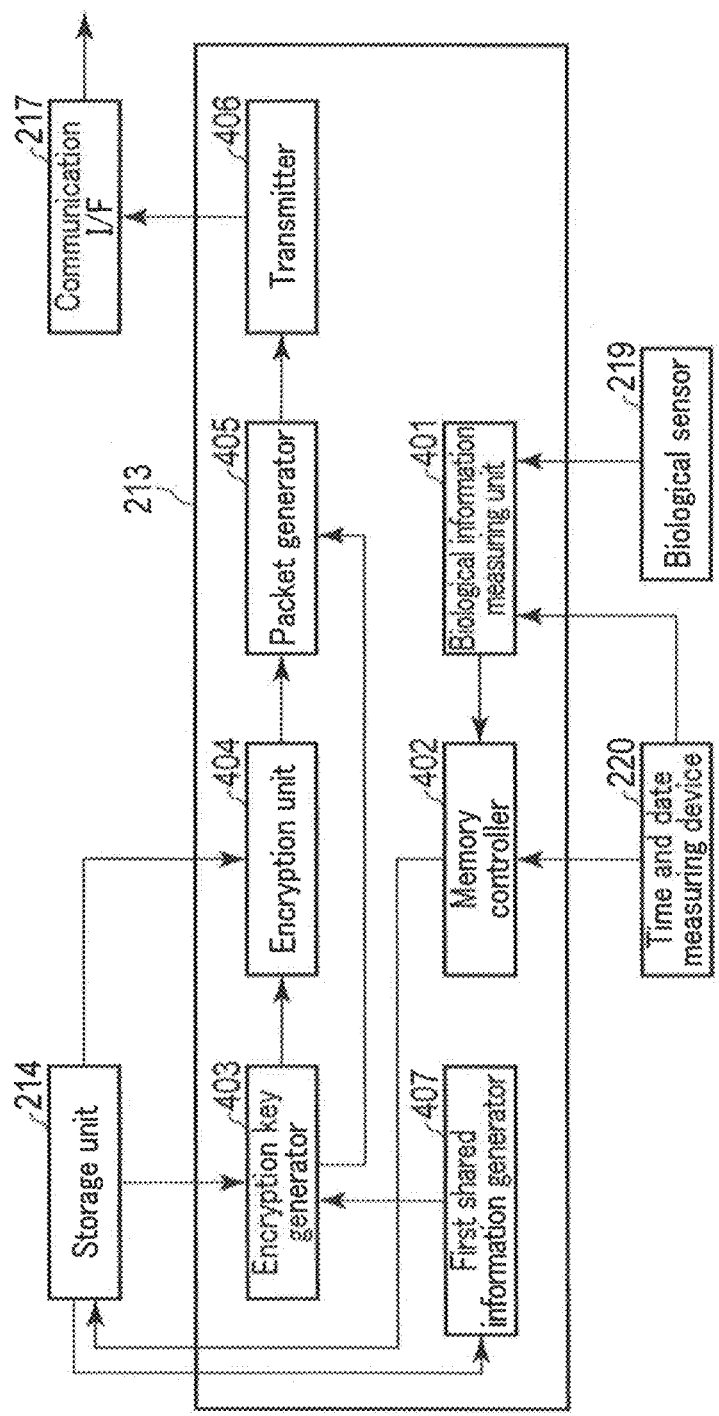
FIG. 4 is a diagram schematically illustrating an exemplary software structure of the data transmitting apparatus according to the embodiment.

Next, an exemplary software structure of the data transmitting apparatus 100 according to the present embodiment will be described with reference to FIG. 4.

When implementing a desired program, the controller 213 of the data transmitting apparatus 100 expands the encryption key generation and packet transmission control program stored in the storage unit 214, into the RAM. The controller 213 interprets and implements with the CPU the encryption key generation and packet transmission control program expanded into the RAM, thereby controlling each structural component. Thus, as shown in FIG. 4, the data transmitting apparatus 100 according to the present embodiment serves as a computer provided with a biological information measuring unit 401, a memory controller 402, an encryption key generator 403, an encryption unit 404, a packet generator 405, a transmitter 406, and a first shared information generator 407.

The biological information measuring unit 401 sends the sensor data that is the biological information detected and output by the biological sensor 219, together with the time/date information acquired from the time and date measuring device 220, to the memory controller 402. The biological information measuring unit 401 may send the time-series data of the biological information in which the biological information and the time/date information are combined, to the memory controller 402.

The memory controller 402 enters into the storage unit 214 the data associated with the sensor data and the time/ date information received from the biological information measuring unit 401. The memory controller 402 may acquire the time/date information from the time and date measuring device 220, and enter the time/date information into the storage unit 214 in association with other received information.

The first shared information generator 407 generates numerical values (event numerical values) relating to quantifiable events. Specifically, the first shared information generator 407 generates, for example, time/date information of the time and date of the data transmitting apparatus measuring an amount relating to the biological information, as an event numerical value.

The encryption key generator 403 generates an encryption key from the first shared information generated by the first shared information generator 407 and the second shared information stored in the storage unit 214. The shared information may be identical numerical values (initial value) stored in advance in the receiving apparatus and transmitting apparatus, and numerical values (event numerical values) relating to a quantifiable event. In particular, the initial value may be information of a specific time and date. In this case, the encryption key generator 403 calculates, for example, the elapsed time period from the initial time and date to the time and date of the event numerical value, and renders this elapsed, time period as an encryption key.

In addition, the encryption key may include other data predetermined and shared with the data receiving apparatus 150, in addition to the shared information. For example, the media access control (MAC) address of the data transmitting apparatus 100 may be contained in advance in the encryption key. This MAC address is also set in advance as a known address in the data receiving apparatus 150. In this case, the MAC address of the data transmitting apparatus 100 is stored in the storage unit 214 and in the storage unit 314.

The encryption unit 404 receives the transmission-targeted data stored in the storage unit 214, and encrypts the targeted data, with the encryption key received from the encryption key generator 403. For the encryption scheme, a common key encryption scheme can be adopted, and is not particularly limited to any specific encryption scheme. Specific examples of the encryption schemes include DES and AES.

The packet generator 405 acquires information regarding the encryption key from the encryption key generator 403, and generates a packet including this encryption key-related information and the targeted data encrypted by the encryption unit 404. This packet is a one-way transmission packet, for example, a BLE advertisement packet. The information relating to the encryption key may include an event numerical value, which is a source of the calculation numerical value included in the encryption key. Specifically, the calculated numerical value included in the encryption key may be an elapsed time period, and the event numerical value may be the time and date of the generation of the encryption key.

The information relating to the encryption key may include the positional information of the sensor. The information of the date and position is used for decoding the data with an encryption key.

The transmitter 406 transmits the packet generated by the packet generator 405 via the communication interface 217 in accordance with a predetermined communication method for one-way transmission. This communication method may be BLE, and the transmitter 406 transmits a packet through the BLE advertising.

<Data Receiving Apparatus>

Figure 5:
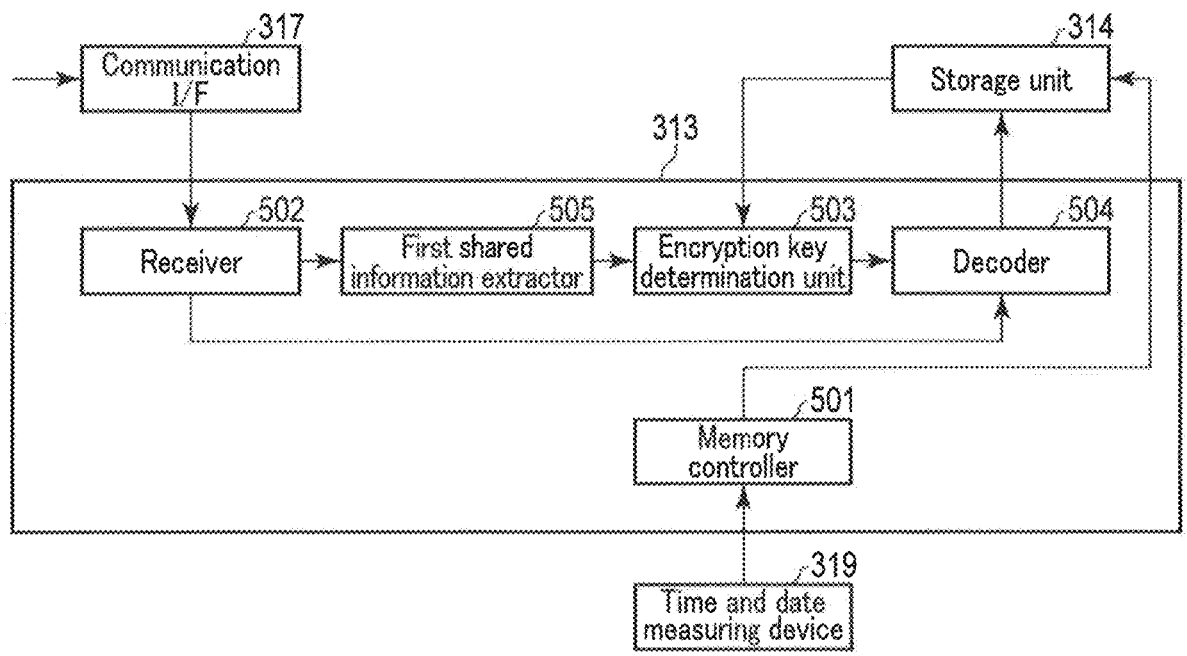
FIG. 5 is a diagram schematically illustrating an exemplary software structure of the data receiving apparatus according to the embodiment.

Next, an exemplary software structure of the data receiving apparatus 150 according to the present embodiment will he described with reference to FIG. 5.

When executing a desired program, the controller 313 of the data receiving apparatus 150 expands the encryption key generation and data decoding control program stored in the storage unit 314 into the RAM. The controller 313 interprets and executes, by the CPU, the encryption key generation and data decoding control program expanded into the RAM, and controls the structural components. Thus, the data receiving apparatus 150 according to the present embodiment functions as a computer including a memory controller 501, a receiver 502, an encryption key determination unit 503, a decoder 504, and a first shared information extractor 505, as shown in FIG. 5.

The memory controller 501 acquires time/date information from the time and date measuring device 319, and stores the time/date information in the storage unit 314 in association with other received information.

The receiver 502 receives a packet from the data transmitting apparatus 100 via the communication interface 317. This packet includes at least the encryption data and information relating to the encryption key.

The first shared information extractor 505 extracts the first shared information included in the packet received by the receiver 502. The first shared information may be the time/date information of the time and date of the measurement of an amount relating to the biological information by the sensor of the data transmitting apparatus.

The encryption key determination unit 503 includes the first shared information generated by the first shared information extractor 505 and the second shared information stored in the storage unit 314 (any identical numerical values shared in advance, serving as an initial value; i.e., any identical numerical values determined in advance between the receiving apparatus and the transmitting apparatus). The first shared information contained in a packet includes, for example, numerical values (event numerical values) relating to a quantifiable event. In particular, an event numerical value may represent the time and date of the measurement of the sensor data by the sensor. An output value obtained through an operation performed when the event numerical value contained in the packet and the initial value stored in the storage unit 314 are input serves as an encryption key. A hash function (that is imperfect) may be adopted for this operation. A perfect hash function may also be adopted for the operation If the packet further contains a MAC address, the encryption key determination unit 503 acquires the MAC address from the storage unit 314. The encryption key determination unit 503 checks whether the MAC address stored in the storage unit 314 matches the MAC address included in the received packet. If a match is established, the encryption key determination unit 503 may proceed with the processing as it is. If a match is not established, the encryption key determination unit 503 discards the packet as being wrongly addressed.

The decoder 504 receives the encryption data from the receiver 502, and further receives the encryption key generated by the encryption key determination unit 503. The decoder 504 decodes the encryption data with this encryption key, and receives the targeted data. The decoder 504 stores the targeted data in the storage unit 314.

<Others>

The functions of the data transmitting apparatus 100 and the data receiving apparatus 150 will be described in detail below in the operation example. According to the present embodiment, the examples are described in which the functions of the data transmitting apparatus 100 and the data receiving apparatus 150 are realized by a general-purpose CPU. However, part or all of the above functions may be realized by one or more dedicated processors. With regard to the functional structure of the data transmitting apparatus 100, functions may be omitted, replaced, and added as appropriate, according to the embodiment.

OPERATION EXAMPLE

<Data Transmitting Apparatus>

Next, an example of the operation of the data transmitting apparatus 100 will be described with reference to FIG. 6. A flowchart illustrating an exemplary processing procedure of the data transmitting apparatus 100 is provided in FIG. 6. The processing procedure described below is merely given as an example, and each of the operations may be modified as needed. Furthermore, steps of the processing procedure described below can be omitted, replaced, and added as appropriate, according to the embodiment.

(Activation)

First, the user activates the data transmitting apparatus 100 so that the activated data transmitting apparatus 100 can implement the encryption key generation and packet transmission control program. In accordance with the processing procedure indicated below, the controller 213 of the data transmitting apparatus 100 generates the first shared information, generates an encryption key based on the first shared information and the second shared information that is shared in advance with the data receiving apparatus, encrypts the transmission-targeted data with the encryption key, and transmits a one-way transmission packet containing the first shared information and encryption data.

(Step S601)

At step S601, the controller 213 functions as the encryption key generator 403 and first shared information generator 407, obtaining, for example, from the storage unit 214 the second shared information (e.g., time/date information of the initial value) shared with the data receiving apparatus, and the first shared information (e.g., time/date information of the measurement of the sensor data by the sensor measuring in the data transmitting apparatus). Then, the encryption key generator 403 calculates an elapsed time period from the time and date of the second shared information to the time and date of the first shared information, thereby generating the information including the elapsed time period as an encryption key.

(Step S602)

At step S602, the controller 213 functions as an encryption unit 404, and encrypts the transmission-targeted data (for example, biological information) with the encryption key determined at step S601 to generate encryption data.

(Step S603)

At step S603, the controller 213 functions as a packet generator 405, generating a packet including the encryption data generated at step S602 and the first shared information (here, the time/date information of the measurement of the sensor data) used for the generation of the encryption key by the encryption key generator 403.

(Step S604)

At step S604, the controller 213 functions as the transmitter 406, transmitting the packet generated at step 3603 through one-side transmission via the communication interface 217. The transmitter 406 may transmit, for example, an advertisement packet via the communication interface 217.

Figure 7:
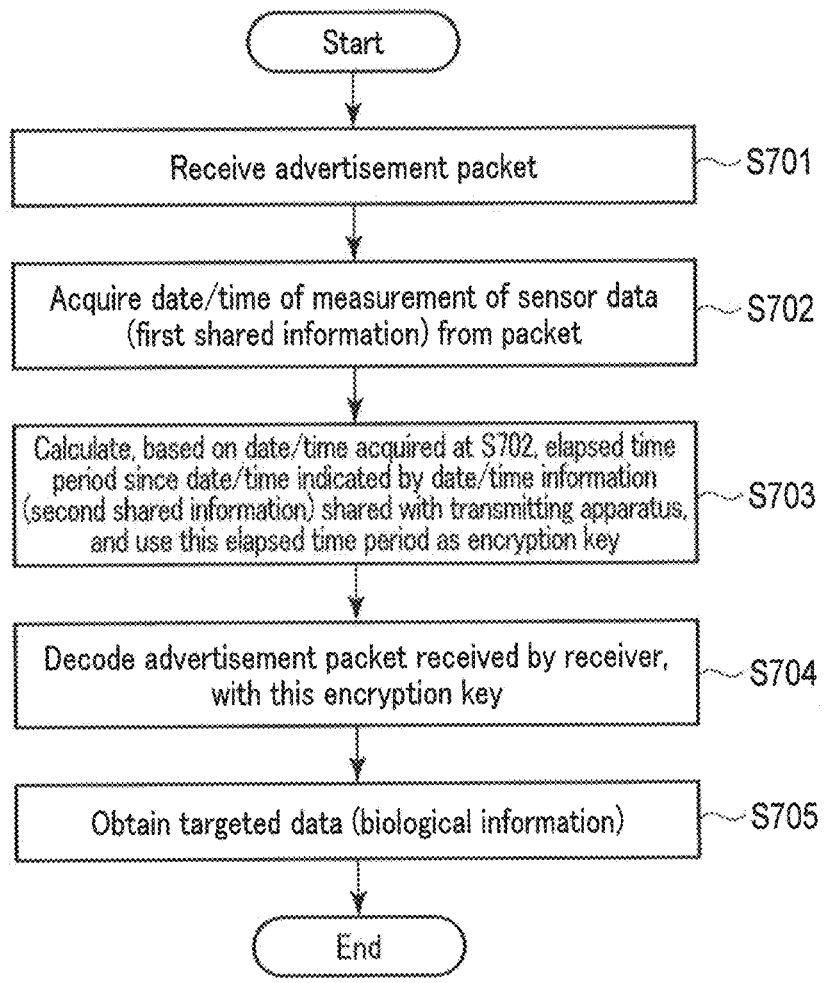
FIG. 7 is a diagram illustrating an exemplary processing procedure of the data receiving apparatus according to the embodiment.

Next, an example of the operation of the data receiving apparatus 150 will be described with reference to FIG. 7. A flowchart illustrating an example of a processing procedure of the data receiving apparatus 150 is provided in FIG. 7. The processing procedure described below is merely given as an example, and each of the operations may be modified as needed. Furthermore, steps of the processing procedure described below can be omitted, replaced, and added as appropriate, according to the embodiment.

(Activation)

First, the user activates the data receiving apparatus 150 so that the activated data receiving apparatus 150 can implement the encryption key generation and data decoding control program. In accordance with the processing procedure below, the controller 313 of the data receiving apparatus 150 generates an encryption key from the first shared information extracted from the received packet and the second shared information stored in advance, decodes the encryption data included in the received packet with the encryption key, and obtains the targeted data contained in the received packet.

(Step S701)

At step S701, the controller 313 functions as a receiver 502, receiving an advertisement packet via the communication interface 317.

(Step S702)

At step S702, the controller 313 functions as the first shared information extractor 505, extracting the first shared information from the packet received at step S701. Here, the first shared information may include the time and date of the measurement of the sensor data.

(Step S703)

At step S703, the controller 313 functions as an encryption key determination unit 503, acquiring from the storage unit 314 the second shared information (time/date information of the initial value that is provided as identical numerical values) shared in advance between the receiving apparatus and the transmitting apparatus. Then, the encryption key determination unit 503 calculates the elapsed time period from the time and date of the initial value to the time and date of the measurement of the sensor data, based on the first shared information acquired at step S702 and the second shared information, and generates this elapsed time period as an encryption key.

If the received packet contains a MAC address, the encryption key determination unit 503 checks whether this address is constant with the MAC address stored in the storage unit 314. If a match is established, the encryption key determination unit 503 may proceed with the processing as is. If a match is not established, the encryption key determination unit 503 discards the packet as being wrongly addressed.

(Step S704)

At step S704, the controller 313 functions as the decoder 504, decoding the advertisement packet received by the receiver 502 with the encryption key generated at step S703.

(Step S705)

At step S705, the controller 313 functions as the decoder 504, acquiring the targeted data decoded at step S704. The targeted data may be biological information acquired by the data transmitting apparatus 100 (e.g., blood pressure value and/or pulse).

<Action and Effects>

As described above, according to the present embodiment, the data transmitting apparatus 100 calculates the elapsed time period from the time and date indicated by the second shared information (the time and date of the initial value) to the time and date indicated by the first shared information (the time and date of the measurement of the sensor data), and generates an encryption key that includes this elapsed time period at step S601. The data receiving apparatus 150 acquires the first shared information, selects the second shared information from the storage unit 314, calculates the elapsed time period, and generates an encryption key at steps S702 and S703. With the same elapsed time period calculated independently by the data transmitting apparatus 100 and by the data receiving apparatus 150, a common encryption key can be possessed on both the transmitting side and the receiving side.

That is, according to the present embodiment, in the data transmitting apparatus 100, the encryption key generator 403 acquires from the storage unit 214 an initial value (second shared information) that is provided as identical numerical values shared in advance between the receiving apparatus and the transmitting apparatus; the first shared information generator 407 generates an event numerical value (first shared information) that is a numerical value relating to a quantifiable event; and the encryption key generator 403 generates an encryption key that includes the second shared information and the numerical value calculated from this second shared information. With this encryption key, the encryption unit 404 can encrypt the transmission-targeted information (e.g., biological information) in accordance with a preset encryption method. The numerical value calculated from the first shared information and the second shared information is data uniquely determined for the data transmitting apparatus and the data receiving apparatus, therefore offering an encryption key with low reproducibility and excellent secrecy. The packet generator 405 generates a packet including the encryption data and first shared information, and the transmitter 406 performs a one-way transmission on this packet (i.e., transmits an advertisement packet).

Thereafter, in the data receiving apparatus 150, the receiver 502 receives the advertisement packet; the first shared information extractor 505 extracts the first shared information from the packet; and the encryption key determination unit 503 acquires the first shared information contained in the packet and the second shared information from storage unit 314. The encryption key determination unit 503 obtains a numerical value from the first shared information and the second shared information through the same calculation as that made by the encryption key generator 403, and generates an encryption key containing information calculated from this numerical value (e.g., elapsed time period). This allows the data transmitting apparatus 100 and the data receiving apparatus 150 to possess identical common encryption keys. Then, the decoder 504 can decode the targeted encryption data received from the receiver 502 with the encryption key generated by the encryption key determination unit 503 to obtain the targeted data. Thus, according to the present embodiment, leakage of the data transmitted by one-way communication is suppressed.

[BLE Advertisement]

The BLE advertisement will be briefly described below.

Figure 8:
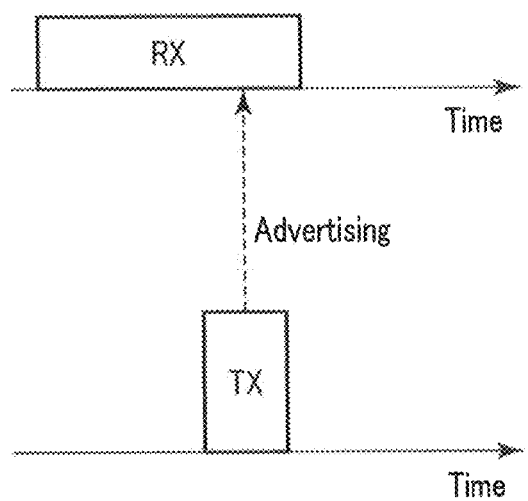
FIG. 8 is an explanatory diagram of advertising performed through BLE.

In the passive scan system adopted in BLE, a new node (corresponding to the data transmitting apparatus 100 of the present embodiment) periodically transmits an advertisement packet informing its presence, as illustrated in FIG. 8. The new node is configured to enter a sleep state of low power consumption after the first transmission of an advertisement packet and before the next transmission, and can therefore save power consumption. Furthermore, the advertisement packet receiving side, which also operates intermittently, consumes a small amount of power associated with the transmission/reception of the advertisement packets.

Figure 9:
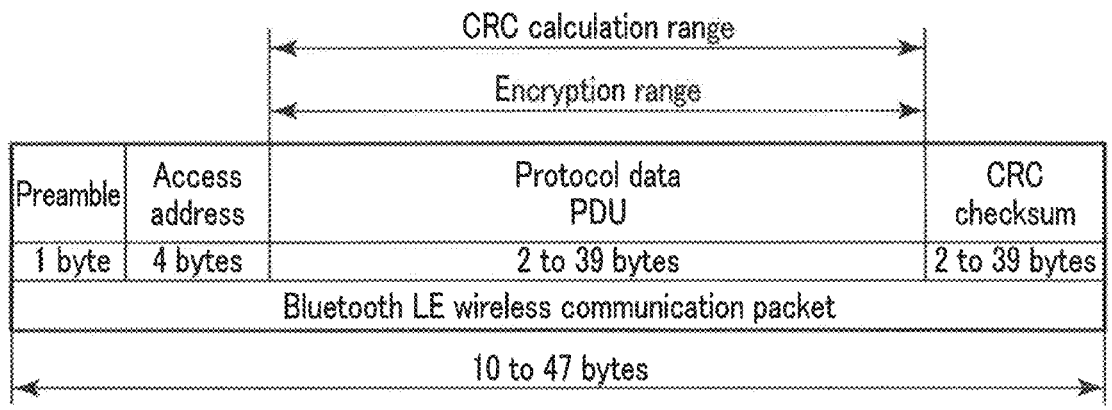
FIG. 9 is a diagram illustrating an exemplary data structure of a packet transmitted and received through BLE.

FIG. 9 shows the basic structure of a BLE wireless communication packet. A BLE wireless communication packet contains a 1-byte preamble, 4-byte access address, 2- to 39-byte (variable) protocol data unit (PDU), and 3-byte cyclic redundancy checksum (CRC). The length of the BLE wireless communication packet is 10 to 47 bytes, depending on the length of the PDU. A 10-byte BLE wireless communication packet (PDU being 2 bytes), also referred to as an "empty PDU packet", is periodically exchanged between the master and the slave.

The preamble field is provided for synchronization of the BLE wireless communication, storing the repetition of "01" or "10". As for the access address, a fixed value is stored for the advertising channel, and an access address of a random number is stored for the data channel. According to the present embodiment, an advertisement packet, which is a BLE wireless communication packet transmitted on an advertising channel, is targeted. The CRC field is used for detection of reception errors. The range of the CRC calculation is limited to the PDU field.

Figure 10:
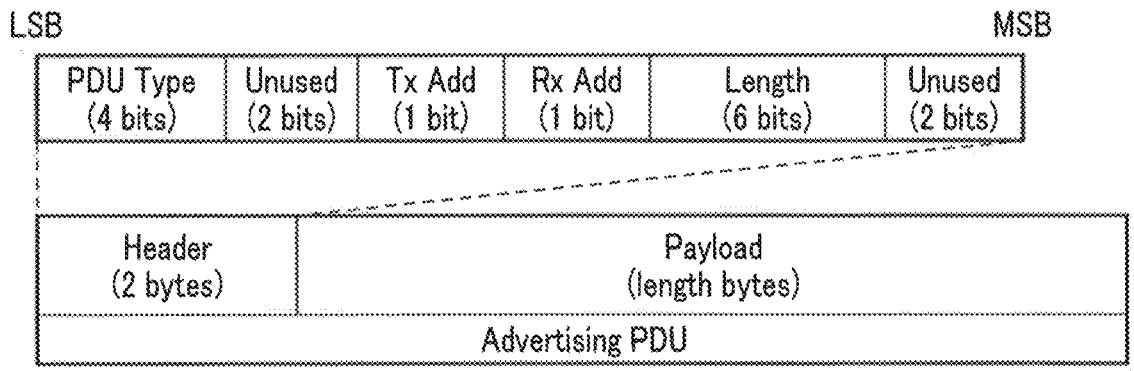
FIG. 10 is a diagram illustrating a data structure of a PDU field of an advertisement packet.

Next, the PDU field of the advertisement packet will be described with reference to FIG. 10. The PDU field of a data communication packet, which is a BLE wireless communication packet transmitted on the data channel, has a data structure that differs from that of FIG. 10. A data communication packet, however, is not targeted in the present embodiment, and therefore the description thereof is omitted.

The PDU field of the advertisement packet includes a 2-byte header and a 0- to 37-byte (variable) payload. Furthermore, the header includes a 4-bit PDU Type field, a 2-bit unused field, a 1-bit TxAdd field, a 1-bit RxAdd field, a 6-bit Length field, and a 2-bit unused field.

A value indicating the type of this PDU is stored in the PDU Type field. Values have been defined such as for "Connectable advertising" and "Disconnected advertising". In the TxAdd field, a flag indicating whether or not a transmission address is included in the payload is stored. Similarly, in the RxAdd field, a flag indicating whether or not a reception address is included in the payload is stored. In the Length field, a value indicating the byte size of the payload is stored.

Any type of data can be stored in the payload. For this reason, the data transmitting apparatus 100 stores the type of sensor data that is to serve as an encryption key, the time and date of the detection of the sensor data, and the encrypted biological information in the payload, using a predetermined data structure. This data structure includes, for example, an identifier specifying the user, an identifier specifying the data transmitting apparatus 100 that is a transmission source device or an identifier representing the data receiving apparatus 150 that is a destination device, time/date data, and biological information associated with the time/date data (e.g., systolic blood pressure value, diastolic blood pressure value, pulse rate, and activity amount).

Figure 11:
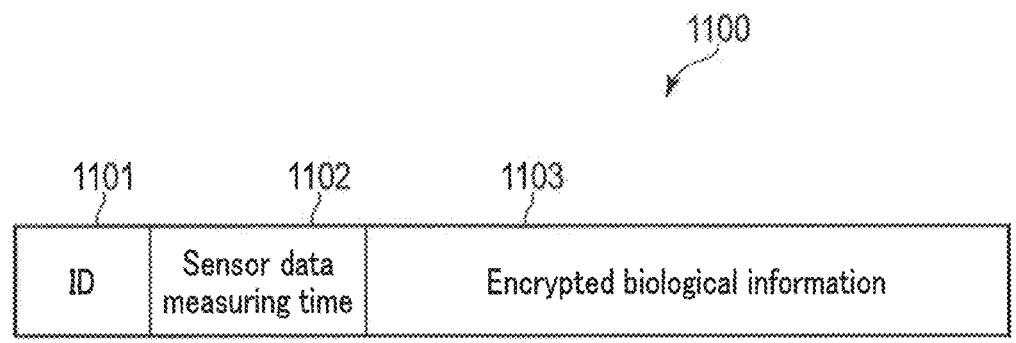
FIG. 11 is a diagram illustrating an exemplary data structure stored in the payload of the PDU field of a packet transmitted by the data transmitting apparatus according to the embodiment.

Next, the data structure of the payload will be described in detail with reference to FIG. 11.

The data structure 1100 includes an ID field 1101, a sensor data measuring time field 1102, and an encryption data field 1103.

An identifier specifying a user is stored in the ID field 1101. In place of, or in addition to, the user specifying identifier, an identifier specifying the data transmitting apparatus 100 or the data receiving apparatus 150 may be stored.

The time/date information of the measurement of the sensor data by the data transmitting apparatus 100 is stored in the sensor data measuring time field 1102.

The transmission-targeted data encrypted with the encryption key corresponding to the time/date information contained in the sensor data measuring time field 1102 is stored in the encryption data field 1103.

MODIFICATION EXAMPLES

The embodiment of the present invention has been described in detail. The above description, however, is given only in the form of examples of the invention in every aspect. Various improvements and modifications can be made without departing from the scope of the present invention. Modifications as described below may be made. In the implementation of the present invention, a specific structure according to the embodiment may be adopted as appropriate. In the following, the same reference numerals are assigned to the same components as in the above embodiment, and the description of the same aspects as in the above embodiment is omitted as appropriate. The following modifications may be combined as appropriate.
<1>
<Examples of System>

An example of a data transmission system including a network will be described with reference to FIG. 12.

In the data transmitting apparatus 100, the packet generator 405 transmits, in an advertisement packet, the first shared information indicating the time and date of the measurement of the sensor data by the data transmitting apparatus 100 and the encryption data encrypted with the encryption key; the data receiving apparatus 150 receives this packet, extracts the first shared information, generates an encryption key based on the first shared information and second shared information, and decodes the encryption data with this encryption key. Thereafter, the data receiving apparatus 150 transmits the decoded data (for example, biological information) to the server 1200 via the network.

The data receiving apparatus 150 performs the transmission to the server 1200, for example, through the mobile communication or WLAN. In the example of FIG. 12, the appearance of a wristwatch-type wearable blood pressure monitor is illustrated as the data transmitting apparatus 100. The appearance of the data transmitting apparatus 100, however, is not limited thereto. The data transmitting apparatus 100 may be a stationary blood pressure monitor, or a sensor device that measures quantities relating to other types of biological information or activity information.
<2>
(Hardware Structure)

In the above embodiment, as shown in FIG. 2, the data transmitting apparatus 100 includes a computer in which an output device 211, an input device 212, a controller 213, a storage unit 214, a drive 215, an external interface 216, a communication interface 217, and a battery 218 are electrically connected to each other. In addition, devices for performing various other kinds of information processing may be provided. The data transmitting apparatus 100 may further include, for example, an atmospheric pressure sensor and a temperature/humidity sensor.

The acceleration sensor detects the movement of the living body, and sends this movement information to the controller 213. The acceleration sensor is, for example, a triaxial acceleration sensor configured to detect the acceleration of the living body with respect to three independent linear axes (e,g., three axes orthogonal to each other). The time and date measuring device 220 outputs an acceleration signal representing the acceleration in three directions to the controller 213.

The barometric sensor detects a barometric pressure, and outputs the barometric pressure data to the controller 213.

The temperature/humidity sensor measures the ambient temperature and humidity of the surroundings of the data transmitting apparatus 100, and outputs the temperature and humidity data to the controller 213.

The data transmitting apparatus 100 may be provided with a GPS receiver. The GPS receiver receives GPS signals transmitted from a plurality of GPS satellites, and outputs the received GPS signals to the controller 213. The controller 213 carries out a distance measurement operation based on these GPS signals, and thereby calculates the information of the current location of the data transmitting apparatus 100, that is, the location of the measurement-target subject (user) wearing the data transmitting apparatus 100.

If this is the case, the battery 218 supplies power, for example, to the output device 211, the controller 213, the storage unit 214, the atmospheric pressure sensor, the temperature/humidity sensor, the communication interface 217, the biological sensor 219, the time and date measuring device 220, and the GPS receiver.

The hardware structure of the above modification may also incorporate a data receiving apparatus 150. If this is the case, the sensor data may contain GPS location information, barometric pressure data, and temperature and humidity data, and an encryption key containing such information may be adopted.
<3>
(Software Structure)

The data transmitting apparatus 100 according to the present embodiment may function as a computer further including an activity amount measurement unit, a step count unit, a sleep state measurement unit, and an environment (temperature and humidity) measurement unit. The storage unit 214 stores, for example, corresponding programs (activity amount measurement program, step count program, sleep state measurement program, and environment (temperature and humidity) measurement program), and, at the implementation of the desired program, this program is expanded into the RAN. The controller 213 interprets and implements, by the CPU, the program expanded into the RAM, and controls the structural components.

The activity amount measurement unit detects the acceleration from the acceleration sensor, and thereby calculates the activity. Through the use of the acceleration signal, the activity amount measurement unit can calculate the activity amount for various activities, including not only walking actions completed by the measurement target subject but also housework actions and desk work actions. The activity amount is an index relating to the activity of the measurement target subject, such as a walking distance, calorie expenditure, or amount of fat burned.

The step count unit detects the acceleration with the acceleration sensor and the atmospheric pressure with the atmospheric pressure sensor, and thereby calculates the number of steps walked, the number of steps walked briskly, and the number of stair-ascending steps. The step count unit calculates the walking of the measurement target subject through the use of the acceleration signal. The step count unit is configured to calculate the number of walking steps, the number of brisk walking steps, and the number of stair ascending steps, and the like, through the use of the atmospheric pressure data and the acceleration signal.

The sleep state measurement unit can estimate the sleep state by detecting the acceleration with the acceleration sensor and the roll-over state with the acceleration signal.

The environment (temperature and humidity) measurement unit stores ambient data indicating the ambient temperature and humidity measured by the temperature/humidity sensor in the storage unit 214, in association with the time of the measurement at the temperature/humidity sensor. The temperature (change in temperature) can be considered as one of the factors for triggering variance in human blood pressure. For this reason, the ambient data is information that may be a determinant of the variance in blood pressure of the measurement target subject.

The software structure of the above modification may also include a data receiving apparatus 150. If this is the case, an encryption key containing information that includes the activity amount, the number of stair-ascending steps, and the sleep state, may be used.

<4>

The data transmitting apparatus 100 is configured as a body separate from the data receiving apparatus 150. The configuration of the data transmitting apparatus 100 and the data receiving apparatus 150, however, is not limited to such an example. A system having the functions of both data transmitting apparatus 100 and data receiving apparatus 150 may be realized by a single computer.

<5>

The data transmitting apparatus 100 may be configured to initiate the measurement of the biological information when the operation unit included in the input device 212 is pressed (switched on). After the measurement is completed, the operation of FIG. 6 may follow.

<6>

In the above-described embodiment, the blood pressure measurement has been described. Blood pressure measurement methods applicable to this embodiment will now be described. General methods include a method of measuring a user's blood pressure value by an oscillometric technique using a cuff structure. The method is not limited to this technique if blood pressure values are the only values to be measured. For example, a pressure pulse wave sensor for detecting the pressure pulse wave for each heartbeat may be provided to detect the pressure pulse wave of the radial artery passing through the measurement site (e.g., the left wrist), thereby measuring the blood pressure value (systolic and diastolic blood pressures) (tonometry method). The pressure pulse wave sensor may measure the blood pressure value by detecting the pulse wave of the radial artery passing through the measurement site (e.g., the left wrist) as a change in impedance (impedance method). The pulse-wave sensor may be provided with a light emitting element for emitting light toward the artery that runs through the corresponding portion of the measurement site and a light receiving element for receiving its reflected light (or transmitted light) to detect the pulse wave as a change in volume for the measurement of the blood pressure value (photoelectric method). The pressure pulse wave sensor may be provided with a piezoelectric sensor in contact with the measurement site to detect a distortion of the artery passing through the corresponding portion of the measurement site under the pressure as a change in electrical resistance for the measurement of the blood pressure value (piezoelectric method). Furthermore, the pressure pulse wave sensor may be provided with a transmission element that transmits a radio wave (transmission wave) toward the artery passing through a corresponding portion of the measurement site and a reception element that receives a reflection wave of the radio wave, to detect a change in the distance between the artery and the sensor due to the pulse wave as a phase shift between the transmission wave and the reflection wave, thereby measuring the blood pressure value (radio wave irradiation method). Any other methods may be applied as long as the physical amount from which the blood pressure value can be calculated is observable.

<7>

The apparatus of the present invention can be realized by a computer and a program. The program can be stored in a recording medium (or storage medium), or provided via a network.

Moreover, each of the devices and device components described above can be carried out either by a hardware structure, or a configuration of the hardware resource and software combined. As the software in the combined configuration, a program for realizing the functions of the apparatuses is adopted, whereby the program is installed in advance from the network or a computer-readable recording medium (or storage medium) into a computer and executed by the processor of the computer.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

In addition, "and/or" represents any one or more of the items listed and connected with "and/or". As a specific example, "x and/or y" represents any element of a set of three elements {(x), (y), (x, y)}. To give another example, "x, y, and/or z" represents any element of a set of 7 elements {(x), (y), (z), (x, y), (x, y, z), (x, y, z)}.

<8>

Furthermore, part or all of the above-described embodiment can be described as in the following additional notes, but is not limited thereto, (Additional Note 1)

A data transmitting apparatus that measures an amount relating to biological information, the data transmitting apparatus comprising a hardware processor and a memory, wherein the hardware processor is configured to:
measure the amount relating to the biological information;
generate, as an encryption key, information calculated from first shared information and second shared information that are shared with a receiving apparatus;
encrypt the biological information with the encryption key and generate encryption data;
generate a one-way transmission packet that includes the first shared information and the encryption data; and
transmit the packet, and the memory comprises:
a storage unit configured to store the first shared information and the encryption data.

(Additional Note 2)

A data receiving apparatus that measures an amount relating to biological information, the data transmitting apparatus comprising a hardware processor and a memory, wherein the hardware processor is configured to
receive encryption data that is data that has been encrypted, and a one-way transmission packet including first shared information shared with a transmitting apparatus;
determine, as an encryption key, information calculated from second shared information shared with the transmitting apparatus, based on the first shared information, and
decode the encryption data included in the packet with the encryption key, and generate decoded data including the biological information measured by the transmitting apparatus, and
the memory includes a storage unit that stores the first shared information and the decoded data.

(Additional Note 3)

A data transmission method comprising:
measuring an amount relating to biological information through use of at least one hardware processor;
generating, as an encryption key, information calculated from first shared information and second shared information that are shared with a receiving apparatus through use of at least one hardware processor;
generating encryption data by encrypting the biological information with the encryption key through use of at least one hardware processor;
generating a one-way transmission packet including the first shared information and the encryption data through use of at least one hardware processor; and
transmitting the packet through use of at least one hardware processor.

(Additional Note 4)

A data, reception method comprising:
receiving a one-way transmission packet including encryption data that is data that has been encrypted and first shared information that can be shared with a transmitting apparatus, through use of at least one hardware processor;
determining, as an encryption key, information calculated from second shared information shared with the transmitting apparatus based on the first shared information through use of at least one hardware processor; and
generating decoded data including biological information measured by the transmitting apparatus by decoding the encryption data included in the packet with the encryption key through use of at least one hardware processor.

What is claimed is:

1. A data transmitting apparatus comprising:
a measurement control unit configured to measure an amount relating to biological information;
an encryption key generation control unit configured to generate, as an encryption key, information calculated from first shared information and second shared information that is shared with a receiving apparatus;
an encryption control unit configured to encrypt the biological information with the encryption key and generate encryption data;
a packet generation control unit configured to generate a one-way transmission packet that includes the first shared information and the encryption data; and
a transmitter configured to transmit the packet,
wherein the information calculated from the first shared information and the second shared information includes an elapsed time period from a time and date determined in accordance with the second shared information to a time and date associated with the first shared information.

2. The apparatus according to claim 1, wherein the first shared information, the second shared information and the calculated information, fail to include the biological information.

3. The apparatus according to claim 2, wherein the encryption key generation control unit associates the first shared information with a time and date, and the second shared information with a predetermined time and date.

4. The apparatus according to claim 3, wherein the time and date associated with the first shared information includes a time and date of measurement of the amount relating to the biological information.

5. The apparatus according to claim 1, wherein the biological information includes at least one of blood pressure values or pulse.

6. A data receiving apparatus comprising:
a receiver configured to receive a one-way transmission packet that includes encryption data that is data that has been encrypted, and first shared information that is shared with a transmitting apparatus;
an encryption key determination control unit configured to determine, as an encryption key, information calculated from second shared information shared with the transmitting apparatus, based on the first shared information; and
a decoding control unit configured to decode the encryption data included in the packet with the encryption key, and generate decoded data,
wherein the decoded data includes biological information measured by the transmitting apparatus, and
the information calculated from the first shared information and the second shared information includes an elapsed time period from a time and date determined in accordance with the second shared information and a time and date associated with the first shared in formation.

7. The apparatus according to claim 6, wherein the first shared information, the second shared information and the calculated information fail to include the biological information.

8. The apparatus according to claim 6, wherein the first shared information is a time and date of measurement of an amount relating to the biological information by the transmitting apparatus, and
the encryption key determination control unit determines the encryption key from the second shared information, based on the time and date of the measurement of the amount relating to the biological information.

9. The data receiving apparatus according to claim 6, wherein the biological information includes at least one of blood pressure values or pulse.

10. A data transmission method comprising:
measuring an amount relating to biological information;
generating, as an encryption key, information calculated from first shared information and second shared information that can be shared with a receiving apparatus;
generating encryption data by encrypting the biological information with the encryption key; and
generating a one-way transmission packet that includes the first shared information and the encryption data; and
transmitting the packet,
wherein the information calculated from the first shared information and second shared information includes an elapsed time period from a time and date determined in accordance with the second shared information to a time and date associated with the first shared information.

11. A data reception method comprising:
receiving a one-way transmission packet that includes encryption data that is data that has been encrypted, and first shared information that is shared with a transmitting apparatus;
determining as an encryption key, information calculated from second shared information shared with the transmitting apparatus, based on the first shared information; and
decoding, with the encryption key, the encryption data included in the packet, and generating decoded data,
wherein the decoded data includes biological information measured by the transmitting apparatus, and
the information calculated from the first shared information and second shared information includes an elapsed time period from a time and date determined in accordance with the second shared information to a time and date associated with the first shared information.

12. A non-transitory computer readable medium storing a computer program which is executed by a computer to provide the steps of:
measuring an amount relating to biological information;
generating, as an encryption key, information calculated from first shared information and second shared information that is shared with a receiving apparatus;
generating encryption data by encrypting the biological information with the encryption key; and
generating a one-way transmission packet that includes the first shared information and the encryption data; and
transmitting the packet,
wherein the information calculated from the first shared information and the second shared information includes an elapsed time period from a time and date determined in accordance with the second shared information to a time and date associated with the first shared information.

13. A non-transitory computer readable medium storing a computer program which is executed by a computer to provide the steps of:
receiving a one-way transmission packet that includes encryption data that is data that has been encrypted, and first shared information that is shared with a transmitting apparatus;
determining as an encryption key, information calculated from second shared information shared with the transmitting apparatus, based on the first shared information; and
decoding, with the encryption key, the encryption data included in the packet, and generating decoded data,
wherein the decoded data includes biological information measured by the transmitting apparatus, and
the information calculated from the first shared information and the second shared information includes an elapsed time period from a time and date determined in accordance with the second shared information to a time and date associated with the first shared information.

* * * * *